United States Patent [19]

Gilligan et al.

[11] Patent Number: 5,780,099
[45] Date of Patent: Jul. 14, 1998

[54] FLOSS YARN BULKING ASSEMBLY AND METHOD

[75] Inventors: Sean G. Gilligan, Kilcullen; Dermot T. Freeman, Killiney, both of Ireland; Larry J. Oliphant, Swisher; Jeffrey S. Meessmann, Iowa City, both of Iowa; Patrick J. Hanley, S. San Francisco, Calif.; Gerald S. Szczech, Iowa City, Iowa

[73] Assignee: Gillette Canada, Inc., Kirkland, Canada

[21] Appl. No.: 677,156

[22] Filed: Jul. 9, 1996

Related U.S. Application Data

[62] Division of Ser. No. 249,515, May 26, 1994, Pat. No. 5,558,901.

[51] Int. Cl.$^6$ ........................................ B05D 3/00
[52] U.S. Cl. .................... 427/175; 427/377; 427/398.2; 427/398.3; 28/281; 57/351
[58] Field of Search .................. 28/281, 252, 258; 57/246, 250, 351; 427/377, 398.1, 398.2, 398.3, 175, 428

[56] References Cited

U.S. PATENT DOCUMENTS

| | | |
|---|---|---|
| 174,619 | 3/1876 | Clark . |
| 290,678 | 12/1883 | Gourdiat . |
| 660,943 | 10/1900 | Bavermeister . |
| 2,667,443 | 1/1954 | Ashton . |
| 2,700,636 | 1/1955 | Ashton . |
| 2,748,781 | 6/1956 | Collat . |
| 3,188,713 | 6/1965 | Dyer et al. ............... 28/281 |
| 3,412,192 | 11/1968 | Clapson . |
| 3,447,296 | 6/1969 | Chidgey et al. ............ 57/245 |
| 3,492,131 | 1/1970 | Schlatter . |
| 3,615,671 | 10/1971 | Shoaf et al. . |
| 3,642,491 | 2/1972 | Schlatter . |
| 3,699,979 | 10/1972 | Muhler et al. . |
| 3,771,536 | 11/1973 | Dragan ................... 132/89 |
| 3,789,858 | 2/1974 | Pesce .................... 132/89 |
| 3,800,046 | 3/1974 | Schlatter . |
| 3,823,449 | 7/1974 | Griset, Jr. ................ 28/1.4 |
| 3,828,419 | 8/1974 | Wanner ................... 29/503 |
| 3,830,246 | 8/1974 | Gillings .................. 132/89 |
| 3,831,233 | 8/1974 | Rendall et al. ............ 28/281 |
| 3,831,363 | 8/1974 | Pike ..................... 28/281 |
| 3,833,975 | 9/1974 | Cahnman et al. ........... 28/281 |
| 3,837,351 | 9/1974 | Thornton . |

(List continued on next page.)

FOREIGN PATENT DOCUMENTS

| | | |
|---|---|---|
| 0 080 440 A1 | 6/1983 | European Pat. Off. . |
| 0 335 466 A2 | 10/1989 | European Pat. Off. . |
| 2 216 803 A | 10/1989 | United Kingdom . |

*Primary Examiner*—Diana Dudash
*Attorney, Agent, or Firm*—William B. Walker

[57] ABSTRACT

A process for manufacturing a continuous dental floss brush comprising alternating portions of thread sections which do not stretch significantly under tension and brush sections which stretch under slight tension, includes the step of coating at least the thread sections of a reverse twisted high tenacity nylon yarn with a solution of polymer in a volatile solvent, the polymer being selected from the group consisting of nylon, polyurethane and mixtures thereof. The thread sections of the yarn are thereafter heated to vaporize solvent therefrom while the yarn is maintained under a tension of from 0.15 to 1N. In the humidifier assembly, having a housing which defines a humidifier zone, the brush sections of the yarn are exposed to a mixture of steam and gas, the steam and gas mixture having a temperature of from 130° C. and a water vapor content of 65% (v/v), while the yarn is under a tension of approximately zero until the brush sections of the yarn have regained at least 100 percent of the diameter of the uncoated, relaxed yarn. Finally the brush sections of the yarn are heated to remove solvent therefrom while the yarn is under a tension of approximately zero to form a floss brush product. As the yarn passes through the humidifier zone, the tension on the yarn is controlled to take account of changes in its length.

4 Claims, 3 Drawing Sheets

U.S. PATENT DOCUMENTS

| | | | |
|---|---|---|---|
| 3,838,702 | 10/1974 | Standish et al. . | |
| 3,879,966 | 4/1975 | Worth et al. | 118/247 |
| 3,896,824 | 7/1975 | Thornton . | |
| 3,897,795 | 8/1975 | Engel . | |
| 3,906,757 | 9/1975 | Arimoto et al. | 68/20 |
| 3,943,949 | 3/1976 | Ashton et al. | 132/89 |
| 3,953,962 | 5/1976 | Breen et al. | 57/140 R |
| 3,972,214 | 8/1976 | Jagersberger | 72/132 |
| 3,991,704 | 11/1976 | Hulstein et al. | 118/2 |
| 4,000,964 | 1/1977 | Newton . | |
| 4,008,727 | 2/1977 | Thornton | 132/89 |
| 4,009,513 | 3/1977 | Andersen | 28/281 |
| 4,013,435 | 3/1977 | Kane et al. | 65/11 W |
| 4,029,113 | 6/1977 | Guyton | 132/91 |
| 4,033,365 | 7/1977 | Klepak et al. | 132/89 |
| 4,047,271 | 9/1977 | Paterson et al. | 28/220 |
| 4,071,615 | 1/1978 | Barth . | |
| 4,073,260 | 2/1978 | Bosworth et al. | 118/8 |
| 4,096,611 | 6/1978 | Heyner | 28/220 |
| 4,142,538 | 3/1979 | Thornton | 132/89 |
| 4,152,886 | 5/1979 | Nelson | 57/208 |
| 4,153,961 | 5/1979 | Cleveland | 8/149 |
| 4,158,976 | 6/1979 | Ditges | 83/157 |
| 4,291,017 | 9/1981 | Beierle et al. . | |
| 4,350,311 | 9/1982 | Pokhodnya et al. | 242/83 |
| 4,414,990 | 11/1983 | Yost | 242/83 |
| 4,548,219 | 10/1985 | Newman et al. | 242/83 |
| 4,571,765 | 2/1986 | Okada et al. | 8/149.3 |
| 4,605,573 | 8/1986 | Deeg et al. | 242/83 |
| 4,627,975 | 12/1986 | Lynch | 242/83 |
| 4,638,823 | 1/1987 | Newman et al. | 242/83 |
| 4,737,904 | 4/1988 | Ominato | 364/167 |
| 4,817,643 | 4/1989 | Olson . | |
| 4,908,153 | 3/1990 | Kossmann et al. | 204/300 EC |
| 4,911,927 | 3/1990 | Hill et al. | 424/443 |
| 4,932,092 | 6/1990 | Yoshida | 8/149 |
| 4,952,392 | 8/1990 | Thame | 424/58 |
| 4,974,615 | 12/1990 | Doundoulakis | 132/32 |
| 4,986,288 | 1/1991 | Kent et al. . | |
| 4,996,056 | 2/1991 | Blass | 424/443 |
| 4,998,978 | 3/1991 | Varum | 132/321 |
| 5,033,488 | 7/1991 | Curtis et al. | 132/321 |
| 5,042,343 | 8/1991 | Boyadjian | 83/208 |
| 5,063,948 | 11/1991 | Lloyd | 132/321 |
| 5,284,169 | 2/1994 | Gilligan et al. | 132/321 |

FLOSS YARN BULKING ASSEMBLY AND METHOD

This application is a division of application Ser. No. 08/249,515 filed May 26, 1994 which application is now U.S. Pat. No. 5,558,901.

FIELD OF THE INVENTION

This invention relates to an improved thin floss brush product and to a novel process for its manufacture. In particular this invention is directed to a process for the manufacture of a continuous yarn having brush sections separated by thinner thread sections.

Tooth decay and dental disease can be caused by bacterial action resulting from the formation of plaque about the teeth and/or the entrapment of food particles between the teeth and interstices therebetween. The removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended.

To improve the effectiveness and convenience of dental flosses, dental flosses combining a thin "floss" portion and a thickened "brush" portion, together with a threader have been developed. The brush portion, when drawn between tooth surfaces, has been found to provide an improved cleaning action which removes materials left by the floss portion, when used alone. The combination provides a substantially superior cleaning action. Such a device is described in U.S. Pat. No. 4,008,727, for example. The complexity of this product requires that each floss segment be individually manufactured and that the product be packaged as bundles of the individual, separate floss articles.

A continuous yarn having brush sections separated by thinner thread sections is disclosed in U.S. Pat. Nos. 4,008,727 and 4,142,538. In the manufacture of brush floss products of this type, a polymer solution can be applied to at least a portion of the yarn and, while the yarn is under sufficient tension to draw it into a thread, heat can be applied to remove the solvent and/or further to polymerize the polymer. The portion of the yarn to which the polymer has been applied remains a thread when the yarn tension is removed after heating. We discovered that conventional textured nylon yarns and previously developed manufacturing processes lacked the tensile strength required for making such a product. Furthermore, the portion of the yarn which was intended to be the brush portion lacked the bulk and texture desired when not under tension.

Attractive and pleasant flavors and flavor odors have been provided in dental products including dental flosses to impart a flavor to the flosses and encourage their regular use. These have been applied in the form of flavoring oils to the surface of floss or wax coatings on the floss, or dispersed in wax coatings applied to the floss. In a process described in copending, commonly assigned application Ser. No. 07/809,625 filed Dec. 17, 1991, now U.S. Pat. No. 5,226,435 flavoring oils are applied to floss in a low-melting wax composition containing a mixture of high and low melting point polyethylene glycols, the low melting characteristic of the wax retaining the flavoring oils without significant loss through evaporation or from oxidation. Application of these low melting wax compositions to a floss brush was found to clog and mat the brush portion of the yarn, reducing its effectiveness as a cleaning article.

We further discovered that conventional textured nylon yarns having brush segments separated by thinner segments typically failed to provide the necessary bulking of the brush segments required for effective cleaning of teeth.

It was also found that the speed at which the yarn could be processed was limited by a number of constraints. Accordingly this invention also addresses the issue of processing a number of yarns simultaneously.

OBJECTS AND SUMMARY OF THE INVENTION

It is one object of this invention to provide on improved floss brush which can be spooled and dispensed as a continuous brush/thread from a traditional floss dispenser.

Another object of this invention is to provide an improved process for the manufacture of a floss brush which can be spooled and dispensed as a continuous brush-thread from a traditional floss dispenser.

A further object of this invention is to provide a process for manufacturing a polymer coated floss brush made from a textured yarn which retains or exceeds the bulk and thickness of the original, uncoated, relaxed yarn.

It is a further object of the invention to provide a humidifier assembly for use in the above process and a process for improving the bulking of the brush sections of the floss brush.

According to the invention there is provided a process for manufacturing a continuous dental floss brush comprising alternating portions of thread sections, which are expanded, and thread sections, the process comprising the steps of a) coating at least the thread sections of a twisted yarn with a solution of polymer in a volatile solvent, the polymer being selected from the group consisting of nylon, polyurethane, and mixtures thereof;

b) heating at least the thread sections of the yarn and vaporizing solvent therefrom while the yarn is maintained under a tension of from 0.15 to 10N; and c) feeding the yarn through a humidifier zone containing a steam and gas mixture, and exposing at least the brush sections of the yarn to the steam and gas mixture, the yarn being maintained at a constant tension which is sufficiently low to allow the brush sections to contract longitudinally until the brush sections of the yarn have regained at least 100 percent of the diameter of the uncoated, relaxed yarn, the yarn being fed into the humidifier zone at a speed greater than that at which the yarn is removed therefrom to maintain a substantially constant brush tension as the brush sections expand in the humidifier zone.

The process may include coating the brush sections with a solution of polymer in a volatile solvent before feeding the yarn through the humidifier zone, the polymer being selected from the group consisting of nylon, polyurethane, and mixtures thereof.

The yarn may be fed into and removed from the humidifier zone by independent drives, the relative speeds of the independent drives being controlled to maintain a substantially constant brush tension as the brush sections expand in the humidifier zone.

The steam and gas mixture may have a temperature of 130° C., and a water vapour content of 65% (v/v).

Preferably the steam and gas mixture is a steam and air mixture having a temperature of 130° C. and a water vapor content of 65% (v/v).

Further according to the invention there is provided a process for restoring the bulk of stretched nylon yarn, comprising feeding the yarn into a humidifier zone containing a steam and gas mixture, the yarn being fed into the humidifier zone at a speed greater than that at which the yarn is removed therefrom to maintain a substantially constant yarn tension as the yarn expands in the humidifier zone.

The steam and gas mixture may have a temperature of 130° C. and a water vapor content of 65% (v/v).

Preferably the steam and gas mixture is a steam and air mixture having a temperature of 130° C. and a water vapor content of 65% (v/v).

The yarn may be fed into and removed from the humidifier zone by independent drives, the relative speeds of the independent drives being controlled to maintain a substantially constant yarn tension as the yarn expands in the humidifier zone.

The yarn passed through the humidifier zone may be supported by a support means as it passes through the humidifier zone. The support means may comprise at least one clamping means which supports the yarn by clamping the yarn as it passes through the humidifier zone, the clamping means being mounted for movement alongside the travelling yarn. The clamping means preferably intermittently releases the yarn as it passes through the humidifier zone, thereby to accommodate reduction in length of the yarn as it passes through the humidifier zone.

The yarn may be guided on rollers as it passes through the humidifier assembly and the process may include chilling at least some of the rollers.

The process may include applying a water/alcohol solution to the rollers.

The yarn may be a yarn coated with a polymer solution.

Still further according to the invention there is provided a humidifier assembly for exposing a yarn to steam, comprising:

a housing defining a humidifier zone, the housing having a yarn inlet and a yarn outlet;

fluid inlet means for introducing a steam and gas mixture into the humidifier zone;

fluid outlet means for removing steam and gas from the humidifier zone; and drive means for feeding the yarn into the humidifier zone at a first speed and removing the yarn from the humidifier zone at a second speed which is less than the first speed, thereby to maintain a substantially constant yarn tension as the yarn expands in the humidifier zone.

The housing and drive means may be designed to accommodate a plurality of yarns simultaneously. The drive means may comprise a plurality of rollers on an input side of the humidifier zone and a plurality of rollers on an output side of the humidifier zone.

The arrangement may include water/alcohol applicator means for applying a water/alcohol solution to circumferential surfaces of at least one of the rollers. The water/alcohol applicator means may include means for applying a water/alcohol solution to the circumferential surfaces of each of the rollers.

The arrangement may include means for stripping excess liquid from the circumferential surfaces of the rollers and means for catching the liquid which is stripped off the circumferential surfaces.

The rollers may have different diameters to accommodate changes in length of the yarn, thereby to control the tension of the yarn.

Separate drive means may be provided for feeding the yarn into the humidifier zone and for removing the yarn from the humidifier zone.

The drive means may include at least one drive motor.

The assembly may include support means for supporting the yarns in the housing as they pass through the humidifier zone.

The support means may be in the form of at least one clamping means for clamping the yarns as they pass through the humidifier zone, each clamping means being mounted for movement alongside the travelling yarns at a speed corresponding to the speed of sections of the yarns which it is clamping.

DETAILED DESCRIPTION OF THE INVENTION

Figure 1:
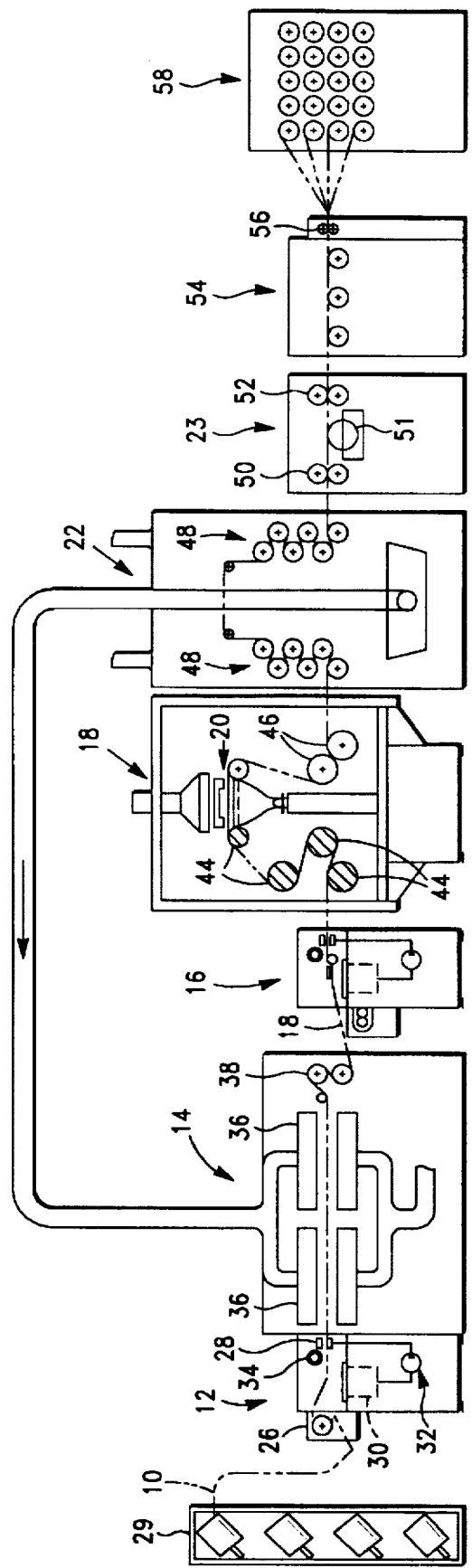
FIG. 1 is a schematic representation of a system for producing a continuous length of connected dental floss brushes in accordance with this invention.

Referring to FIG. 1, a process for manufacturing a floss brush from a yarn includes passing a length of yarn 10 through a dye/resin applicator assembly 12, drying the dye/resin in a drying chamber 14, passing the yarn 10 through a resin applicator assembly 16, bulking or expanding the fiber 10 in a humidifier assembly 18 which defines a humidifier zone 20, drying the yarn in a second drying chamber 22 and then passing the yarn 10 through a wax/flavoring reservoir 23.

The untreated yarn 10 is supported on creels 24 from where it is feed by a tensioner 26 to the dye/resin applicator assembly 12 which is described in greater detail in copending, commonly assigned patent application entitled "yarn coating assembly and method", the entire contents of which are incorporated herein by reference.

The applicator assembly 12 includes an applicator head 28 supplied with a coating material, e.g. dye or resin or a combination thereof from a supply tank 30 via a pump 32. A cam (not shown) mounted on a wheel 34 controls the intermittent coating of the yarn by periodically urging the yarn into contact with the coating material supported by the head 28.

In order to dry the dye/resin, the yarn is passed into the drying chamber 14 where heated air from the second drying chamber 22 and heat generated by infrared heaters 36 mounted within the drying chamber 14, dry the yarn 10 before it passes to the resin applicator assembly 16. Drive rollers 38 mounted on the downstream side of the drying chamber 14 serve to draw the yarn 10 through the dye/resin applicator assembly 12 and drying chamber 14 while the tensioner 26, in the form of a disc brake, insures that the requisite tension is maintained on the yarn 10. Downstream of the drive rollers 38 the tension of the yarn 10 is significantly reduced and remains at this lower level as it passes through the resin applicator assembly 16 and into the humidifier assembly 18. The resin applicator assembly 16, while similar to the dye/resin applicator assembly 12, includes a tension sensing means for sensing the yarn tension.

As the yarn 10 passes through the humidifier zone 20 of the assembly 18, the yarn 10 is exposed to a steam and gas mixture, which in this embodiment is a steam/air mixture, and which is used in the bulking process, as is described in greater detail hereinafter.

Upstream of the humidifier zone 20, the yarn 10 is fed over a number of rollers 44 which are driven by a first drive means (not shown) which is common to the drive means driving the drive rollers 38.

In contrast, the rollers 46 on the downstream side of the humidifier zone 20 are driven by a second drive means (also not shown).

The use of a second drive means is necessitated by the fact that the yarn, as it passes through the humidifier zone 20, bulks and therefore contracts resulting in a change in the speed of the yarn 10 as it passes through the zone 20.

Upon exiting the humidifier assembly 18, the yarn 10 passes through the drying chamber 22 where it is fed along a circuitous path over a number of rollers 48.

A second set of drive rollers 50, also driven by the second drive means, maintains the requisite tension on the yarn 10 as the yarn 10 passes into the wax/flavoring reservoir 23. Wax/flavoring is applied to the yarn 10 by means of a lick roller 51. A pair of squeeze rollers 52, mounted on the downstream side of the reservoir 23, squeezes excess wax/flavoring from the yarn 10 before the yarn passes into a refrigeration unit 54. A chiller drive roller pair 56 driven by a third drive means (not shown) draws the yarn 10 from the refrigeration unit 54 whereafter the yarn is taken up on low tension take-up winders 58.

It will be appreciated that the various drive means may include separate drive motors or may share a common drive motor to which they are connected by suitable gearing arrangements.

As indicated on FIG. 1 a plurality of yarns may be arranged next to each other and processed simultaneously before being taken up on the respective low tension take-up winders 58.

Figure 2:
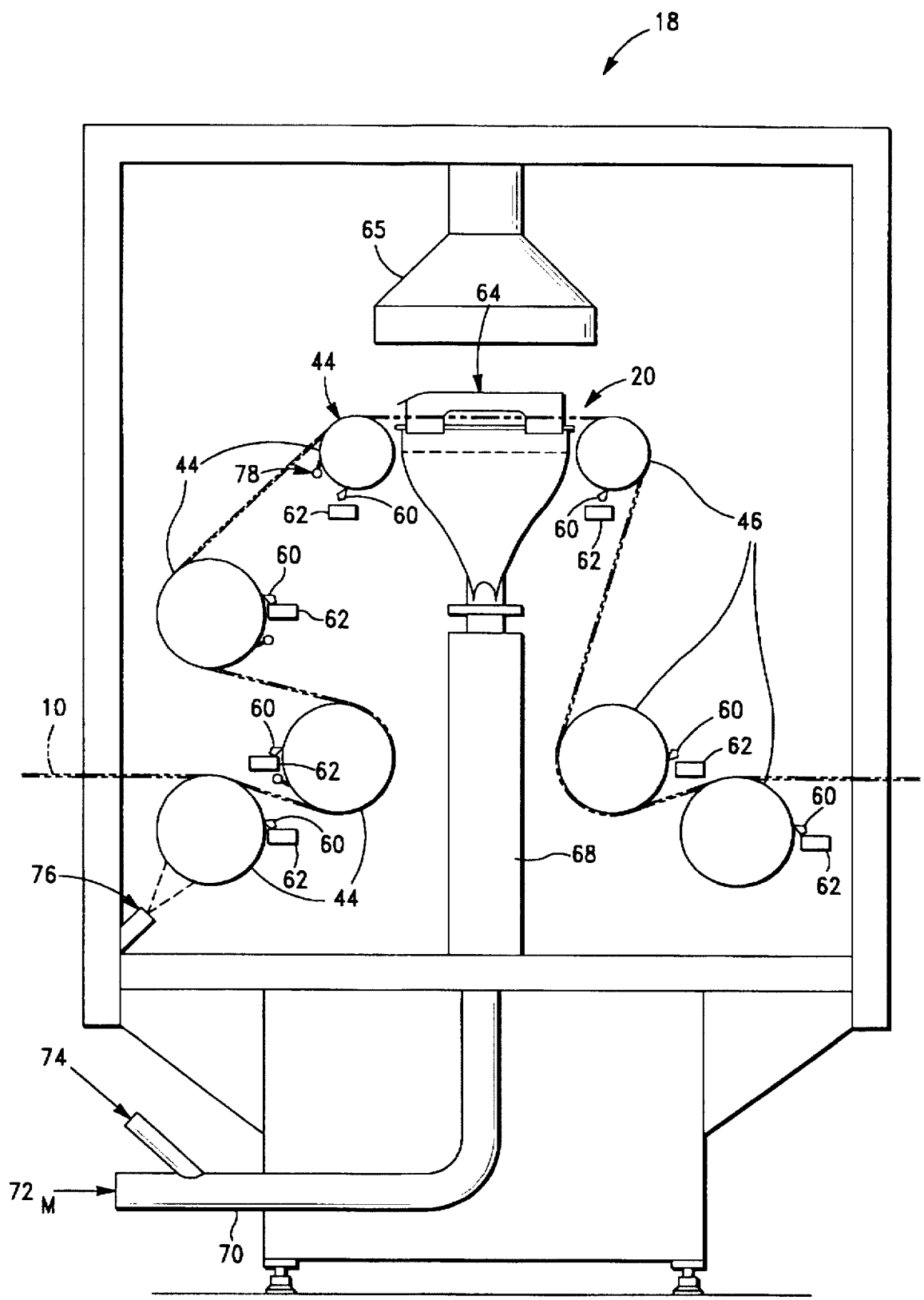
FIG. 2 is a schematic side view of a humidifier assembly for use in the system of FIG. 1, in accordance with the invention.

The humidifier assembly 18 is shown in greater detail in FIG. 2, the rollers 44, 46 serving to guide the yarn 10 through the assembly 18. Each of the four rollers 44 on the upstream side as well as the three rollers 46 on the downstream side are provided with doctor blades 60 to avoid excessive build up of moisture on the rollers by stripping excess liquid off the circumferential surfaces of the rollers. The moisture is then caught in drip pans 62 associated with each of the doctor blades 60 and led off by means of conduits (not shown).

The humidifier zone 20 is defined intermediate a steam/gas diverter 64, an exhaust hood 65, and a distribution cone 66. The exhaust hood 65 serves as an outlet means for steam and gas. The gas which is removed could include air and alcohol fumes, the alcohol eminating from a sprayer as is described in greater detail below. The cone 66, which supplies steam/gas to the zone 20, is connected by means of a steam manifold 68 to an inlet conduit 70, which serves as an inlet means for the steam/gas mixture. The conduit 70, in turn, splitting into a steam inlet 72 and a hot air inlet 74. The hot air inlet 74 supplies heated air at a temperature of approximately 400° C. thus maintaining the zone 20 at an elevated temperature. The first five rollers, in contrast, are refrigerated to a temperature of 5° C. by means of cold water swivels. As can be seen in FIG. 2 a sprayer 76 and a felt pad 78 are provided, these serving to apply a water/alcohol solution to the first and fourth rollers respectively. Cooling of the rollers and the use of the water/alcohol solution avoids adhesion of the yarn 10 to the rollers. For this embodiment, a 50% Isopropyl alcohol/50% water solution was found to work well. It will be appreciated that any number of the rollers could be cooled or treated with the water/alcohol solution.

As the yarn 10 passes through the humidifier zone 20 the heated air/steam mixture causes the yarn 10 to fluff up/bulk and consequently to contract. The steam, air and any alcohol vapors, having passed through the zone 20, are drawn off by the exhaust hood 65.

Figure 3:
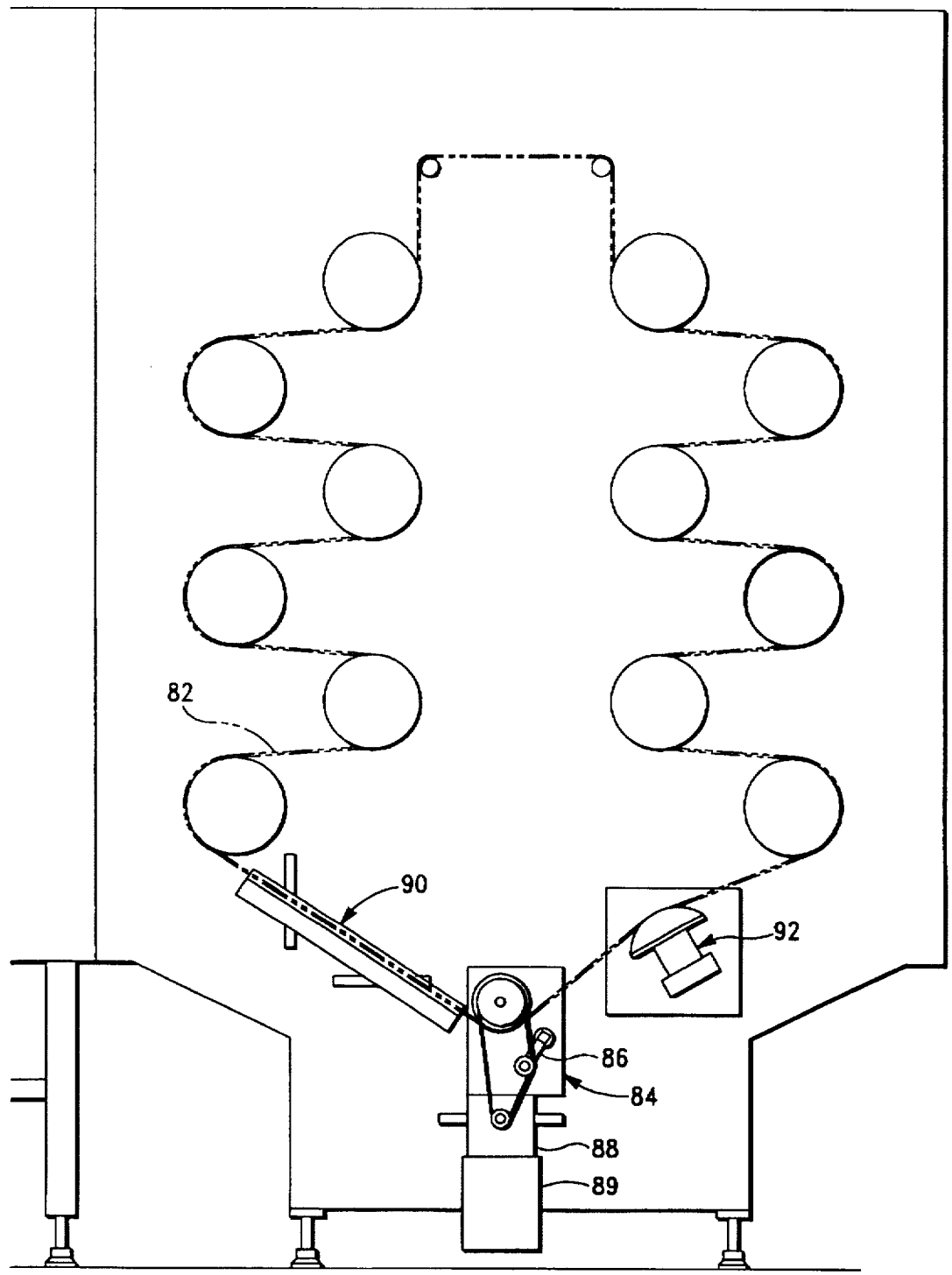
FIG. 3 is a schematic side view of another embodiment of the humidifier assembly in accordance with the invention.

Another embodiment of the humidifier assembly 18 is illustrated in FIG. 3 which provides a set of 7 downstream rollers and a set of 7 upstream rollers. The illustration does not show the rollers themselves but merely provides a schematic representation of the path of a drive chain 82 for driving the rollers. The chain 82 is driven from a drive mount 84 which includes a chain tensioner 86, and a gear box 88 mounted on a gear mount 89. As shown in FIG. 3, the lower ends of the chain 82 are supported by a chain guide 90 and a spann box 92, respectively, to provide added support to the chain 82 as it enters and exits its drive path on either side of the drive mount 84. In this embodiment the entire housing 93 forms the humidifier zone and the rollers (not shown) have different diameters to take account of changes in length of the yarn.

Although preferred embodiments of the invention have been described in some detail, it is to be understood that obvious variations can be made without departing from the spirit and scope of the invention as defined by the appended claims.

The invention claimed is:

1. A process for restoring the bulk of stretched nylon yarn comprising feeding the yarn into a humidifier zone containing a steam and gas mixture, the yarn being fed into the humidifier zone at a speed greater than that at which the yarn is removed therefrom to maintain a substantially constant yarn tension as the yarn expands radially in the humidifier zone, wherein the yarn is guided on rollers as it passes through the humidifier assembly, and the process includes applying a water/alcohol solution to the rollers.

2. A process of claim 1 for restoring the bulk of stretched nylon yarn wherein the yarn is fed into and removed from the humidifier zone by independent drives.

3. A process of claim 2 for restoring the bulk of stretched nylon yarn wherein the relative speeds of the independent drives are controlled to maintain a substantially constant yarn tension as the yarn expands in the humidifier zone.

4. A process of claim 3 including chilling at least one of the rollers.

* * * * *